United States Patent
Barkoczy et al.

(10) Patent No.: US 7,960,375 B2
(45) Date of Patent: Jun. 14, 2011

(54) 8-CHLORO-2,3-BENZODIAZEPINE DERIVATIVES

(75) Inventors: Jozsef Barkoczy, Budapest (HU); Istvan Ling, Budapest (HU); Gyula Simig, Budapest (HU); Gabor Szenasi, Budapest (HU); Gabor Gigler, Budapest (HU); Szabolcs Kertesz, Budapest (HU); Gyula Szücs, Budapest (HU); Geza Szabo, Budapest (HU); Miklos Vegh, Budapest (HU); Laszlo Gabor Harsing, Budapest (HU)

(73) Assignee: Egis Gyogyszergyar Rt., Budapest (HU)

( * ) Notice: Subject to any disclaimer, the term of this patent is extended or adjusted under 35 U.S.C. 154(b) by 818 days.

(21) Appl. No.: 10/567,598

(22) PCT Filed: Jul. 29, 2004

(86) PCT No.: PCT/HU2004/000082
§ 371 (c)(1),
(2), (4) Date: Feb. 20, 2008

(87) PCT Pub. No.: WO2005/012265
PCT Pub. Date: Feb. 10, 2005

(65) Prior Publication Data
US 2008/0153814 A1    Jun. 26, 2008

(30) Foreign Application Priority Data
Aug. 4, 2003 (HU) .................... 0302449

(51) Int. Cl.
*A61P 9/10* (2006.01)
*A61K 31/55* (2006.01)
*C07D 243/02* (2006.01)

(52) U.S. Cl. .................... 514/221; 540/567
(58) Field of Classification Search .......... 514/221; 540/567
See application file for complete search history.

(56) References Cited

U.S. PATENT DOCUMENTS

| | | | |
|---|---|---|---|
| 4,322,346 A | 3/1982 | Korosi et al. | 260/239 |
| 4,614,740 A | 9/1986 | Lang et al. | 514/221 |
| 4,840,948 A | 6/1989 | Lang et al. | 514/221 |
| 6,200,970 B1 | 3/2001 | Ling et al. | 514/221 |

FOREIGN PATENT DOCUMENTS

| | | |
|---|---|---|
| FR | 2566774 | 1/1986 |
| WO | WO 9211262 | 7/1992 |

*Primary Examiner* — Brenda L Coleman
(74) *Attorney, Agent, or Firm* — Jonathan Myers; Andrew Wilford

(57) ABSTRACT

The invention relates to new 8-chloro-2,3-benzodiazepine derivatives of the general formula (I), wherein R stands for a lower alkyl group or a group of the general formula —NH—R', wherein R' stands for a lower alkyl or a lower cycloalkyl group), and pharmaceutically acceptable acid addition salts thereof. The invention also encompasses a process for the preparation of said compounds, pharmaceutical compositions containing them and new intermediates useful for the preparation of the new 8-chloro-2,3-benzodiazepine derivatives. The compounds according to the invention possess AMPA/kainate receptor inhibiting activity.

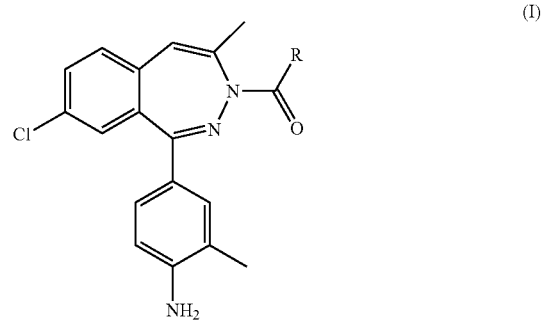

12 Claims, No Drawings

8-CHLORO-2,3-BENZODIAZEPINE DERIVATIVES

CROSS REFERENCE TO RELATED APPLICATIONS

This application is the US national phase of PCT application PCT/HU2004/000082 filed Jul. 29, 2004 with a claim to the priority of Hungarian patent application P0302449 itself filed Aug. 4, 2003.

FIELD OF THE INVENTION

The invention relates to new 8-chloro-2,3-benzodiazepine derivatives possessing AMPA/kainate receptor inhibiting activity, a process for the preparation thereof, pharmaceutical compositions containing said new benzodiazepine derivatives and the use of said compounds for the treatment or prevention of diseases. The invention also encompasses new intermediates useful for the preparation of the new 8-chloro-2,3-benzodiazepine derivatives.

TECHNICAL BACKGROUND OF THE INVENTION

It is known that 2,3-benzodiazepines exert anxiolytic, antidepressant, anticonvulsive, muscle relaxant and neuroprotective activities (e.g. Hungarian patent specifications Nos. 155572, 179018, 191698, 191702, 195788 and 206719, international patent specification No. WO/01422 etc.).

It is also known that certain 2-,3-benzodiazepine derivatives exert their activity by inhibiting AMPA receptors in a non-competitive manner [Donovan S. D. et. al.: J. Pharmacol. Exp. Ther. 271, 25-29, (1994)].

It is known that glutamate receptors of AMPA type play an important role in acute and chronic diseases of the central nervous system; thus, by inhibiting AMPA receptors muscle relaxant, neuroprotective and anticonvulsive effects can be achieved.

DETAILED DESCRIPTION OF THE INVENTION

According to an aspect of the present invention there are provided 8-chloro-2,3-benzodiazepine derivatives of the general formula

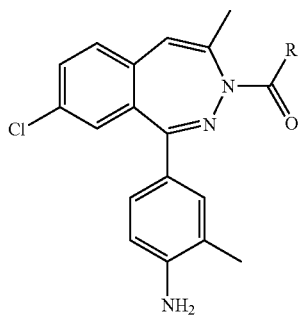

(I)

wherein
R stands for a lower alkyl group or a group of the general formula —NH—$R^1$, wherein
$R^1$ stands for a lower alkyl or a lower cycloalkyl group), and pharmaceutically acceptable acid addition salts thereof.

The interpretation of the terms used throughout this specification is as follows:

The term "lower alkyl" is intended to mean straight chained or branched, saturated alkyl groups having preferably 1 to 6 carbon atom(s), (e.g. methyl, ethyl, n-propyl, isopropyl, n-butyl group etc.)

The term "lower cycloalkyl" refers to cyclic hydrocarbon groups having 3 to 7 carbon atoms (cyclopropyl, cyclobutyl, cyclopentyl or cyclohexyl group etc.)

The term "pharmaceutically acceptable acid addition salts" relates to salts formed with pharmaceutically acceptable acids, which salts possess the biological properties of the corresponding base of general formula (I). For the salt formation both inorganic or organic acids may be applied (such as hydrogen chloride, hydrogen bromide, sulfuric, phosphoric, nitric, formic, acetic, lactic, malic, tartaric, succinic, citric, maleic, fumaric, toluenesulfonic, benzenesulfonic acids and the like).

To a subgroup of the compounds according to the invention belong the compounds of the general formula (I) containing in the place of R a lower alkyl, preferably an alkyl having 1 to 4 carbon atom(s), particularly methyl or ethyl, furthermore pharmaceutically acceptable salts thereof.

Another subgroup of the compounds according to the invention is represented by the compounds of general formula (I), wherein R stands for an —NH—$R^1$ group, in which formula $R^1$ represents 1-4 alkyl or 3-6 cycloalkyl, particularly methyl or cyclopropyl, furthermore pharmaceutically acceptable salts of these compounds.

Particularly preferred representatives of the compounds according to the invention are the following derivatives:
1-(4-amino-3-methylphenyl)-8-chloro-4-methyl-3H-2,3-benzodiazepine-3-carboxylic acid methyl amide,
1-(4-amino-3-methylphenyl)-8-chloro-4-methyl-3H-2,3-benzodiazepine-3-carboxylic acid cyclopropyl amide,
3-acetyl-1-(4-amino-3-methylphenyl)-8-chloro-4-methyl-3H-2,3-benzodiazepine,
3-propionyl-1-(4-amino-3-methylphenyl)-8-chloro-4-methyl-3H-2,3-benzodiazepine,
and pharmaceutically acceptable acid addition salts of these compounds.

According to another aspect of the present invention there is provided a process for the preparation the compounds of general formula (I), wherein
R stands for a lower alkyl group or a group of the general formula —NH—$R^1$, wherein
$R^1$ stands for a lower alkyl or a lower cycloalkyl group) and pharmaceutically acceptable acid addition salts thereof, which comprises
a) reducing a compound of the general formula (II),

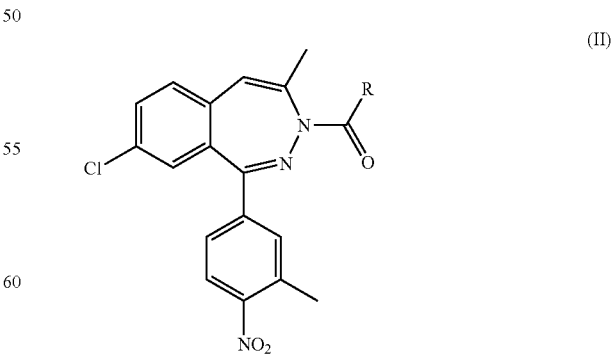

(II)

wherein R is as stated above; or
b) for the preparation of the compounds of general formula (I) containing in the place of R a group of the general formula —NH—R¹, wherein R¹ is as stated above (that is compounds of the general formula (III),

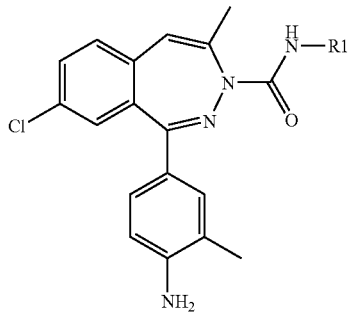

(III)

wherein R¹ is as stated above), reacting a compound of the general formula (IV),

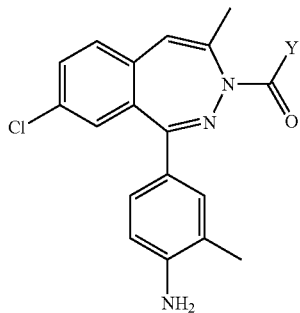

(IV)

wherein Y stands for lower alkyl or a leaving group, with an amine of the general formula (V),

H₂N—R1  (V)

wherein R¹ is as stated above,
and, if desired, converting the compound of the general formula (I) thus obtained into a pharmaceutically acceptable acid addition salt thereof.

According to variant a) of the process according to the invention a compound of the general formula (II), wherein R is as stated above, is reduced. This reaction can be carried out by methods known per se. According to an embodiment of the process a catalytic hydrogenation is performed. As catalyst e.g. Raney nickel, palladium applied onto a carrier or platinum may be used. As hydrogen source hydrogen, hydrazine, hydrazine hydrate, formic acid, trialkyl ammonium formates or alkali metal formates may serve. As reducing agent stannic (II) chloride or sodium dithionite may also be applied.

According to variant b) of the process according to the invention a compound of the general formula (IV) is reacted with an amine of the general formula (V) to form a compound of the general formula (II)—that is a compound of the general formula (I) containing a —NH—R¹ group in the place of R. In the general formula (IV) Y stands for lower alkyl or a leaving group. The leaving group is preferably a halogen atom (e.g. bromine or iodine), an aryloxy group (e.g. an optionally substituted phenoxy group, preferably a phenoxy group) or a lower alkoxy group (e.g. methoxy, ethoxy group, etc.). The process may be carried out by methods known per se as described in the literature [Houben-Weyl: Amine, vol. XI., Georg Verlag, Stuttgart, (1957); S. Patai: The chemistry of amine group, Interscience Publishers, (1968)].

The reaction may be performed in a protic solvent (preferably in lower alkanols, particularly in ethanol) or in the excess of the amine of general formula (V). The reaction is carried out at a temperature between –20° C. and 150° C., preferably between 20° C. and 60° C.

If desired, the thus-obtained compounds of the general formula (I) may be converted into pharmaceutically acceptable acid addition salts thereof. The salt formation is performed by methods known per se. The inorganic or organic acid used for the salt formation is added to a solution of the compound of general formula (I) in an inert organic solvent, or a solution of the acid used for the salt formation in an inert organic solvent is applied.

The compounds of general formula (II) used as starting substances for the process according to the invention have not so far been described in the literature.

According to a further aspect of the present invention there are provided new compounds of the general formula (II), wherein R is as stated above.

According to a still further aspect of the present invention there are provided compounds of the general formula (VIII),

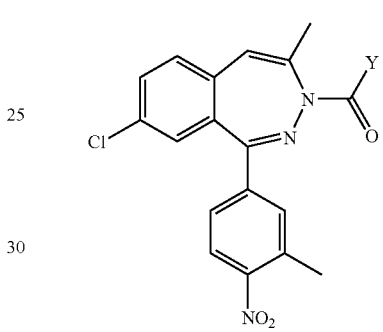

(VIII)

wherein Y stands for a leaving group.

According to a still further aspect of the present invention there is provided a process for the preparation of compounds of the general formula (II), wherein R is as stated above, which comprises reacting the compound of the formula (VII),

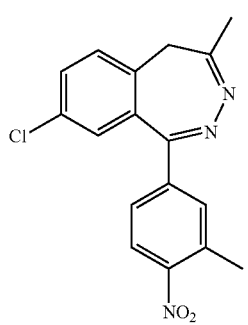

(VII)

with a reagent capable of introducing an Y group, and reacting the thus-obtained compound of the general formula (VIII) with an amine of the general formula (V).

In the first step of the process a compound of the general formula (VIII), wherein Y stands for a lower alkyl group or a leaving group, is formed from the 2,3-benzodiazepine of the formula (VII) by reacting it with a reagent capable of introducing the Y group. Y represents a lower alkyl group or a leaving group. The leaving group is preferably a halogen atom (e.g. bromine or iodine), an aryloxy group (e.g. an optionally substituted phenoxy group, preferably a phenoxy group) or a lower alkoxy group (e.g. methoxy, ethoxy group etc.). The process can be carried out by methods known per se as described in the literature [Houben-Weyl: Methoden der Organischen Chemie, Carbonsäure und Carbonsäure-derivative, Band E5; S. Patai: The chemistry of amides, Interschience Publishers, (1970)]. Thus, in case of the compounds containing as leaving group a phenoxy group in the place of Y the acylation is preferably carried out with phenyl chloroformate, in the presence of a base (preferably an organic base, such as triethyl amine), at the boiling point of the reaction mixture. In case of the compounds containing an alkyl in the place of Y the reaction is preferably carried out with an appropriate carboxylic anhydride (e.g. acetic anhydride or propionic anhydride) at a temperature between 100° C. and 150° C. The carboxylic anhydride may also serve as reaction medium, usually there is no need to use another solvent.

The thus-obtained compound of the general formula (VIII) is then interacted with an amine of the general formula (V). The reaction is performed as specified above in connection with the compounds of general formula (IV) with the amines of general formula (V).

The compounds of the general formula (I)—as it was mentioned above—possess valuable pharmaceutical properties and may be used particularly for the treatment and prevention of central nervous system disorders, which can be treated by the administration of AMPA/kainate receptor inhibitors. The following indications are specifically mentioned: epilepsy, diseases involving muscle spasticity, stroke, accidents involving cerebral and spinal lesions, sclerosis multiplex, Guillain-Barre syndrome, motoneuron disease (ALS), Parkinson disease and other neurodegenerative disorders.

According to a still further aspect of the present invention there are provided pharmaceutical compositions comprising as active ingredient a compound of the general formula (I), wherein R is as stated above, or a pharmaceutically acceptable acid addition salt thereof in admixture with suitable inert solid or liquid carriers and/or auxiliary agents, and if desired, further pharmaceutically active ingredients.

According to a still further aspect of the present invention there is provided a process for the preparation of the pharmaceutical compositions specified above, which comprises admixing a compound of the general formula (I) or a pharmaceutically acceptable acid addition salt thereof with inert solid or liquid pharmaceutical carriers and/or auxiliary agents and, if desired, with further pharmaceutically active ingredients, and bringing the mixture to galenic form.

The pharmaceutical compositions according to the invention may be prepared by methods conventionally applied in the pharmacological industry.

The pharmaceutical compositions of the present invention may be suitable for oral (e.g. tablets, coated tablets, capsules, pills, solutions, suspensions or emulsions), parenteral (e.g. injection solutions for intravenous, intramuscular or intraperitoneal use), rectal (e.g. suppositories) or local (e.g. ointments) administration. The solid or liquid pharmaceutical compositions may be produced by methods conventionally applied in the pharmaceutical industry.

The solid pharmaceutical compositions for oral administration may comprise binding agents (such as gelatine, sorbite, polyvinyl pyrrolidone, etc.), carriers (such as lactose, glucose, starch, potassium phosphate), tabletting auxiliaries (e.g. magnesium stearate, talc, polyethylene glycol, silicon dioxide, etc.) and wetting agents (e.g. sodium lauryl sulphate).

The pharmaceutical compositions for oral administration may be e.g. solutions, suspensions or liquid emulsions containing e.g. suspending agents (e.g. gelatine, carboxymethyl cellulose, etc.), emulsifying agents (e.g. sorbitan monooleate, etc.), solvents (e.g. water, oils, glycerine, propylene glycol, ethanol) and preservers (e.g. methyl p-hydroxybenzoate, etc.).

The pharmaceutical compositions for parenteral administration are generally sterile solutions of the active ingredient in water or in isotonic sodium chloride solution.

The pharmaceutical compositions for rectal administration (e.g. suppositories) contain the active ingredient dispersed in a basic material (e.g. cocoa butter, etc.) usually applied for the preparation of suppositories.

The pharmaceutical compositions according to the invention may be prepared by methods conventionally applied in the pharmacological industry. The compound of general formula (I) or a pharmaceutically acceptable acid addition salt thereof is admixed with inert solid or liquid pharmaceutical carriers and auxiliary agents and the mixture is brought to galenic form. Different pharmaceutical formulations and preparations thereof are described e.g. in Remington's Pharmaceutical Sciences, 18$^{th}$ Edition, Mack Publishing Co., Easton, USA, (1990).

The pharmaceutical compositions of the present invention usually contain 0.1-95.0% by mass of the compound of general formula (I), a pharmaceutically acceptable acid addition salt or quaternary ammonium derivative thereof. The daily dose of the compounds of general formula (I) depends on several factors, e.g. on the activity of the active ingredient, the way of administration, the severity of the disease to be treated, the patient's general condition, age and body weight. The oral dose for adults is generally 0.5-1000 mg, preferably 20 to 200 mg/day, which may be administered to the patients in one or more portion(s). In case of emergency a single dose of 10-1000 mg may be administered.

Glutamate is the most important stimulant neuron transmitter in the central nervous system. The effects of glutamate are mediated by receptors of NMDA, AMPA and kainate type connected to the ion channel. Non-competitive inhibitors of AMPA/kainate receptors with a 2,3-benzodiazepine structure exhibit a significant muscle relaxant, neuroprotective and anticonvulsive effect, so potentially they can be applied in case of all diseases wherein the inhibition of AMPA/kainate receptors proves to be favourable. Such diseases are e.g. epilepsy, disorders involving muscle spasticity, different neurodegenerative diseases, stroke, etc.

Surprisingly it has been found that the potency of non-competitive AMPA antagonistic effect of the 2,3-benzodiazepines having the general formula (I) is unchanged, their toxicity shown during prolonged administration is, however, negligible.

Methods:

"Spreading Depression" Test in Chicken Retina

The study was performed according to Sheardown (1993). Chickens (Shaver Redbrow, 4 to 7 days old) were anaesthetised with diethyl ether and decapitated. The eyes were enucleated and cut along the equatorial plane. The anterior part and the vitreous body were removed, the posterior parts of the eyes were placed in Ringer solution of the following composition: NaCl 100 mM, KCl 3 mM, $CaCl_2$ 1 mM, $MgSO_4$ 1 mM, $NaHCO_3$ 30 mM, D-glucose 10 mM, pH 7.3). After a stabilization period of 90 minutes latency of spreading depression (SD) induced by 5 µM S-AMPA was measured at room temperature.

The first reading of latency was the control value. Then, retinas were incubated for 15 minutes in Ringer solution containing the test compound, and latency of SD was measured again in the presence of the test compound. Following incubation of retinas in drug-free Ringer solution for 60 minutes SD was measured in order to assess the degree of recovery from the drug effect. Prolongation of the latency of spreading depression by 30 seconds or more was regarded as 100% inhibition.

REFERENCE

Sheardown, M. J., 1993. The triggering of spreading depression in the chicken retina: A pharmacological Study. Brain Res. 607, 189-194

Maximal Electroshock (MES) Test in Mice

The experiments were performed according to Swinyard et al. (1952). Male NMRI mice weighing 20 to 25 g were treated intraperitoneally with the test compounds administered in a volume of 10 ml/kg. Thirty minutes later an electroshock of 50 Hz, 40 mA, 0.4 seconds was applied through corneal electrodes, and the presence or absence of tonic extensor convulsion of the hind legs was observed in all mice. The reaction was positive if the animals showed tonic extensor convulsions in the hind legs, the reaction was negative if this response did not occur. The number of animals showing positive reaction was counted in each group. The dose of test substance causing 50% ($ED_{50}$) inhibition was calculated according to the method of Litchfield and Wilcoxon (1949).

REFERENCES

Litchfield, J. T., Wilcoxon, F., 1949. A simplified method of evaluating dose-effect experiments. J. Pharmacol. Exp. Ther. 96: 99-113 (1949), Swinyard, E. A., Brown, W. C., Goodman, L. S., 1952. Comparative assays of antiepileptic drugs in mice and rats. J. Pharmacol. 106, 319-330 (1952).

Permanent Focal Cerebral Ischemia in Mice

In these experiments a modified method of Karkoutly et al. (1990) was used. Male NMRI mice weighing 30-35 g were anaesthetized with 2,2,2-tribromoethanol at 500 mg/kg (20 ml/kg) administered i.p. The surgical procedure was performed according to Welsh et al. (1987). After drilling a hole into the skull the distal branch of the middle cerebral artery was electrocoagulated. Test compounds were administered i.p. 30 min after surgery. Two days later the animals were deeply anaesthetized with sodium pentobarbital (120 mg/kg i.p.). The brain was perfused through the left ventricle of the heart with a 4% solution of 2,3,5-triphenyltetrazolium chloride (TTC). One hour later the animals were decapitated, the brains were removed and placed into ice-cold saline for a few min. Then the brains were fixed in 8% formalin solution for 24 hours. The necrotic (non-stained with TTC) brain surface area was measured by means of an image analyser computer system (DigiCell for Windows 4.0). Statistical significance was assessed using ANOVA followed by Duncan's test.

Results 1-(4-amino-3-methyl-phenyl)-8-chloro-4-methyl-3-methylcarbamoyl-3H-2,3-benzodiazepine statistically significantly decreased the necrotic surface area already at a dose of 0.3 mg/kg i.p., while the reference compound, 7-acetyl-5-(4-aminophenyl)-8-methyl-7H-1,3-dioxolo-[4,5-h][2,3]-benzodiazepine produced a similar effect only at 10 mg/kg ip. (Table 1).

Table 1

Neuroprotective effect of 1-(4-amino-3-methyl-phenyl)-8-chloro-4-methyl-3-methylcarbamoyl-3H-2,3-benzodiazepine in permanent focal ischemia model in mice

| Compound | Dose (mg/kg ip.) | | | | |
|---|---|---|---|---|---|
| | 0.1 | 0.3 | 1.0 | 3.0 | 10.0 |
| 1-(4-amino-3-methylphenyl)-8-chloro-methyl-3-methyl-carbamoyl-3H-2,3-benzodiazepine | −5 | −17* | −17* | −15* | −22* |
| 7-acetyl-5-(4-amino-phenyl)-8-methyl-7H-1,3-dioxolo-[4,5-h][2,3]benzodiazepine | — | — | −1 | −14 | −21* |

*$p < 0.05$

Pharmacological testing of 7-acetyl-5-(4-aminophenyl)-8-methyl-7H-1,3-dioxolo-[4,5-h][2,3]benzodiazepine, a non-chiral compound with a chemical structure similar to those of the compounds of the general formula (I) according to the present invention, demonstrated that efficacy of 1-(4-amino-3-methyl-phenyl)-8-chloro-4-methyl-3-methylcarbamoyl-3H-2,3-benzodiazepine, a compound provided by the present invention, has improved in a surprisingly great extent in the neuroprotective test. This could not be expected at all. Based on the above results, the compounds of the general formula (I) according to the present invention with 2,3-benzodiazepine chemical structure can be especially suitable for the treatment of diseases of the brain characterized by neuronal loss, primarily stroke, brain and spinal cord injury, multiple sclerosis, Guillain-Barre syndrome, motoneurone disease (ALS), Parkinson's disease and other neurodegenerative disorders, etc.

REFERENCES

Karkoutly, C., Backhauss, C., Nuglisch, J., Krieglstein, J.: The measurement of the infarcted area after middle cerebral artery occlusion in the mouse: a screening model. In Krieglstein, J., Oberpichler, H. ed. Pharmacology of Cerebral Ischemia 1990. Wissenschaftliche Verlagsgesellschaft mbH Stuttgart. 63-69 (1990).

Welsh, F. A., Sakamoto, T., McKee, A., Sims, R. E.: Effect of lactacidosis on pyridine nucleotide stability during ischemia in mouse. J. Neurochem. 49:846-851 (1987).

Study of Toxic Effects in Rats

The study was performed in female Wistar rats. On the day preceding the first treatment all animals were weighed and randomly allocated into treatment groups (10 animals/group). The test compounds were suspended in 0.4% hydroxymethyl cellulose solution (Methocell F4 M, Daw Chemical Company, USA) and were administered orally once a day for 7 days. The dose of non-chiral compounds according to the examples 8 and 9 was 15 mg/kg/day.

Animals of the control group were treated with the vehicle. The weight of the animals was registered every day. Weight gain was the difference between body weights on the first day and last day of the experiment. Toxicity of the test compounds was shown as a decrease in body weight or negative weight gain.

Results are shown in Table 2.

TABLE 2

| Compound No. of Example | SD, $ED_{50}$ μM | MES, $ED_{50}$ mg/kg ip. | BWG g |
|---|---|---|---|
| 8 | 2.5 | 4.1 | 9.9 ± 3.1 |
| 9 | 0.8 | 2.2 | 17.7 ± 1.3 |
| Control | — | — | 17.4 ± 1.4 |

SD=spreading depression (in chicken retina): The AMPA receptor agonist S-AMPA induces a slowly progressing change in optical density starting from the edge of the eyecup and spreading over the whole retina. AMPA/kainate receptor antagonist can slow this process down.

MES=maximal electroshock (in mice): electroshock of sufficient current intensity applied through corneal electrodes to mice causes tonic extensor convulsion of the hind legs.

BWG=body weight gain: the difference between body weights on the first and last days of the experiment given as mean ± standard error of the mean.

The above results demonstrate that the 2,3-benzodizepine derivatives of the present invention produce the usual in vitro and in vivo effects characteristic for AMPA/kainate receptor inhibitors. On the other hand, the compounds of the present invention practically did not alter body weight gain when administered to female Wistar rats for 7 days, that is these compounds caused no toxic effect. These results indicate that the compounds of formula (I) produced strong AMPA/kainate antagonist effects while their toxic effect was almost negligible during long-term administration.

The compounds of the present invention can be useful for the treatment of central nervous system disorders in which the pathophysiological role or dysfunction of the glutamatergic system is proven or postulated and the inhibition of AMPA/kainate receptors is advantageous. Thus, the 2,3-benzodiazepine derivatives of the present invention can be used effectively for the treatment of central nervous system disorders in which administration of the inhibitors of AMPA/kainate receptors is beneficial for reaching or maintaining a therapeutic action. The compounds of the general formula (I) can be administered especially in the following therapeutic indications: epilepsy, spastic rigidity, stroke, brain and spinal cord traumas, multiple sclerosis, Guillan-Barre syndrome, motoneuron disease (ALS), Parkinson's disease, and other neurodegenerative disorders.

According to a still further aspect of the present invention there is provided the use of the compounds of general formula (I) and pharmaceutically acceptable acid addition salts thereof as a pharmaceutical ingredient.

According to a still further aspect of the present invention there is provided a process for the treatment of central nervous system disorders by the administration of compounds possessing AMPA/kainate receptor inhibiting activity, which comprises administering to a patient in need of such treatment a pharmaceutically effective amount of a compound of the general formula (I) or a pharmaceutically acceptable salt thereof.

Further details of the present invention are to be found in the following Examples without limiting the scope of protection to the said Examples.

EXAMPLE 1

3-Acetyl-8-chloro-4-methyl-1-(3-methyl-4-nitrophenyl)-3H-2,3-benzodiazepine

A solution of 1.5 g (4.6 mmoles) of 8-chloro-4-methyl-1-(3-methyl-4-nitrophenyl)-5H-2,3-benzodiazepine in 15 ml of acetic anhydride is stirred in an oil bath of 130 to 140° C. for 5 hours. The reaction mixture is poured onto about 200 g of crushed ice and the separated crystals are filtered off. The crude product is recrystallized from acetonitrile. Thus 0.78 g (46%) of the desired compound melting at a temperature of 192 to 194° C. is obtained.

Elementary analysis: $C_{19}H_{16}ClN_3O_3$ (369.81)

Calculated: C, 61.71%, H, 4.36%, N, 11.36%, Cl, 9.59%.
Found: C, 60.02%, H, 4.53%, N, 11.08%, Cl, 9.71%.

IR (KBr) 1681, 1527, 1333, 1309.

$^1$H-NMR (DMSO-$d_6$) δ 8.06 (d, J=8.4 Hz, 1H), 7.66 (dd, J1=2.2 Hz, J2=8.4 Hz, 1H), 7.63 (~s, 1H), 7.50 (m, 2H), 7.20 (~s, 1H), 6.65 (s, 1H), 2.55 (s, 3H), 2.22 (s, 3H), 2.17 (s, 3H).

$^{13}$C-NMR (DMSO-$d_6$) δ 169.00, 150.24, 145.85, 140.50, 137.83, 134.34, 133.95, 133.18, 131.37, 130.77, 130.31, 130.07, 128.95, 124.80, 123.70, 22.05, 19.48, 19.22.

EXAMPLE 2

8-Chloro-4-methyl-1-(3-methyl-4-nitrophenyl)-3-propionyl-3H-2,3-benzodiazepine

A solution of 1.78 g (5.4 mmoles) of 8-chloro-4-methyl-1-(3-methyl-4-nitrophenyl)-5H-2,3-benzodiazepine in 18 ml of propionic anhydride is stirred in an oil bath of 130 to 140° C. for 4 hours. The reaction mixture is poured onto about 100 g of crushed ice, extracted first with 50 ml, then twice with 20 ml each of dichloromethane. The organic phase is washed first with 30 ml of saturated sodium carbonate, then three times with 30 ml each of water and dried over anhydrous sodium sulfate. The gum obtained after evaporation is purified by column chromatography, and the crude product is recrystallized from ethanol. Thus 1.01 g (49%) of the desired compound melting at 134-138° C. is obtained.

Elementary analysis: $C_{20}H_{18}ClN_3O_3$ (383.84)

Calculated: C, 62.58%, H, 4.73%, N, 10.95%, Cl, 9.24%.
Found: C, 62.06%, H, 4.76%, N, 10.85%, Cl, 9.14%.

IR (KBr) 1676, 1521, 1349.

$^1$H-NMR (DMSO-$d_6$) δ 8.07 (d, J=8.4 Hz, 1H), 7.68 (dd, J1=2.2 Hz, J2=8.4 Hz, 1H), 7.62 (d, J=1.4 Hz, 1H), 7.52 (d, J=8.2 Hz, 1H), 7.49 (dd, J1=1.6 Hz, J2=8.3 Hz, 1H), 7.20 (d, J=2.1 Hz, 1H), 6.65 (s, 1H), 2.65 (m, 2H), 2.55 (s, 3H), 2.17 (d, J=0.7 Hz, 3H), 1.03 (m, 3H).

$^{13}$C-NMR (DMSO-$d_6$) δ 150.25, 140.53, 137.82, 134.38, 133.90, 133.18, 131.35, 130.74, 130.30, 129.98, 128.92, 124.80, 123.65, 123.04, 26.81, 19.49, 19.24, 8.61.

EXAMPLE 3

8-Chloro-4-methyl-1-(3-methyl-4-nitrophenyl)-3H-2,3-benzodiazepine 3-carboxylic acid phenyl ester 15 g (45.7 mmoles) of 8-chloro-4-methyl-1-(3-methyl-4-nitrophenyl)-5H-2,3-benzodiazepine are boiled in a mixture of 28.85 ml (228.5 mmoles) of phenyl chloroformate and 6.34 ml (45.7 mmoles) of triethylamine for 3.5 hours. The reaction mixture is diluted with 150 ml of cyclohexane, the solvent is decanted off the separated oily product, the residue is dissolved in dichloromethane, washed first with saturated sodium hydrogen carbonate solution, then with water and dried over anhydrous sodium sulfate. After evaporation the crude product is recrystallized from ethanol. Thus 11.86 g (58%) of the desired compound (yellow) melting at 188-190° C. are obtained.

Elementary analysis: $C_{24}H_{18}ClN_3O_4$ (447.877)

Calculated: C, 64.36%, H, 4.05%, N, 9.38%, Cl, 7.92%.
Found: C, 64.16%, H, 4.01%, N, 9.33%, Cl, 7.90%.

IR (KBr) 3440, 1730, 1333, 1209.

$^1$H-NMR (CDCl$_3$) δ 7.98 (d, J=8.5 Hz, 1H), 7.64 (d, 1H), 7.50 (dd, J1=2.1 Hz, J2=8.5 Hz, 1H), 7.15-7.46 (m, 8H), 6.43 (q, J=0.9 Hz, 1H), 2.63 (s, 3H), 2.39 (d, J=1.2 Hz, 3H).

$^{13}$C-NMR (CDCl$_3$) δ 166.99, 151.01, 150.89, 150.49, 144.91, 140.58, 137.55, 134.51, 134.37, 133.91, 131.73, 131.28, 130.23, 130.15, 129.38, 128.78, 125.75, 124.69, 123.61, 121.57, 20.27, 19.93.

EXAMPLE 4

8-Chloro-4-methyl-1-(3-methyl-4-nitrophenyl)-3H-2,3-benzodiazepine-3-carboxylic acid methyl amide 11.86 g (26.4 mmoles) of 8-chloro-4-methyl-1-(3-methyl-4-nitrophenyl)-3H-2,3-benzodiazepine-3-carboxylic acid phenyl ester are stirred with a solution of 43 ml of methylamine (~8M) in ethanol at room temperature for 24 hours. The separated crystals are filtered off and washed with ethanol. Thus 8.87 g (87%) of the desired compound (yellow) melting at 196-198° C. are obtained.

Elementary analysis: C$_{19}$H$_{17}$ClN$_4$O$_3$ (384.821)
Calculated: C, 59.30%, H, 4.45%, N, 14.56%, Cl, 9.21%.
Found: C, 57.73%, H, 4.35%, N, 14.06%, Cl, 9.01%.
IR (KBr) 3383, 1670, 1515, 1344, 853.
$^1$H-NMR (CDCl$_3$) δ 8.00 (d, J=8.2 Hz, 1H), 7.41. (m, 3H), 7.20 (d, J=8.2 Hz, 1H), 6.99 (d, J=2.1 Hz, 1H) 6.22 (s, 1H), 6.06 (bq, J=4.3 Hz, 1H), 2.97 (d, J=4.9 Hz, 3H), 2.64 (s, 3H), 2.24 (d, J=0.9 Hz, 3H).
$^{13}$C-NMR (CDCl$_3$) δ 166.55, 156.30, 150.18, 148.15, 140.89, 138.49, 135.02, 133.91, 133.65, 131.12, 131.01, 130.02, 129.65, 128.18, 124.83, 121.57, 26.91, 20.40, 19.78.

EXAMPLE 5

8-Chloro-4-methyl-1-(3-methyl-4-nitrophenyl)-3H-2,3-benzodiazepine-3-carboxylic acid cyclopropyl amide 2.07 g (4.6 mmoles) 8-chloro-4-methyl-1-(3-methyl-4-nitrophenyl)-3H-2,3-benzodiazepine-3-carboxylic acid phenyl ester are boiled in 10 ml of cyclopropylamine for 10 hours. The separated crystals are filtered off, and the crude product is re-crystallized from ethanol. Thus 1.12 g (59%) of the desired compound melting at 221-223° C. is obtained.

Elementary analysis: C$_{21}$H$_{19}$ClN$_4$O$_3$ (410.867)
Calculated: C, 61.39%, H, 4.66%, N, 13.64%, Cl, 8.63%.
Found: C, 61.27%, H, 4.65%, N, 13.62%, Cl, 8.54%.
IR (KBr) 3404, 1675, 1516, 1344, 849.
$^1$H-NMR (DMSO-d$_6$) δ 8.00 (d, J=8.4 Hz, 1H), 7.80 (d, J=1.1 Hz, 1H), 7.62 (dd, J1=2.2 Hz, J2=8.4 Hz, 1H), 7.59 (dd, J1=1.7 Hz, J2=8.5 Hz, 1H), 7.44 (d, J=8.5 Hz, 1H), 7.14 (d, J=2.2 Hz, 1H), 7.08 (bd, J=2.6 Hz, 1H), 6.45 (s, 1H), 2.60 (m, 1H), 2.54 (s, 3H), 2.12 (s, 3H), 0.65 (m, 2H), 0.59 (m, 2H).
$^{13}$C-NMR (DMSO-d$_6$) δ 166.53, 156.16, 150.00, 147.66, 140.47, 138.45, 135.46, 134.16, 132.97, 130.93, 130.39, 129.98, 129.37, 129.14, 124.49, 121.91, 23.20, 19.44 (2C), 6.47.

EXAMPLE 6

3-Acetyl-1-(4-amino-3-methylphenyl)-8-chloro-4-methyl-3H-2,3-benzodiazepine 0.78 g (2.1 mmoles) of 3-acetyl-8-chloro-4-methyl-1-(3-methyl-4-nitrophenyl)-3H-2,3-benzodiazepine are dissolved in the mixture of 15 ml of methanol and 15 ml of dichloromethane, and about 0.5 g of wet Raney-nickel catalyst and 0.26 ml (5.25 mmoles) of 98% hydrazine hydrate are subsequently added to it under vigorous stirring. The mixture is stirred for further 1 hour. The catalyst is filtered off, washed with dichloromethane, the filtrate is evaporated and the residue is solidified by rubbing with 15 ml of water. The crude product is recrystallized from ethanol. Thus 0.56 g (79%) of the desired compound melting at 209-211° C. is obtained.

Elementary analysis: C$_{19}$H$_{18}$ClN$_3$O (339.83)
Calculated: C, 67.16%, H, 5.34%, N, 12.37%, Cl, 10.43%.
Found: C, 65.87%, H, 5.46%, N, 12.21%, Cl, 10.26%.
IR (KBr) 3388, 3344, 3236, 1646, 1388.
$^1$H-NMR (DMSO-d$_6$) δ 7.60 (dd, J1=2.3 Hz, J2=8.4 Hz, 1H), 7.45 (d, J=8.4 Hz, 1H), 7.26 (d, J=2.2 Hz, 1H), 7.13 (~s, 1H), 6.95 (dd, J1=1.8 Hz, J2=8.2 Hz, 1H) 6.61 (d, J=8.3 Hz, 1H) 6.58 (s, 1H), 5.55 (bs, 2H), 2.16 (s, 3H), 2.10 (s, 3H), 2.06 (s, 3H).
$^{13}$C-NMR (DMSO-d$_6$) δ 171.00, 168.15, 150.08, 146.10, 137.84, 135.80, 131.89, 130.42, 130.32, 129.57, 129.47, 123.35, 122.82, 120.55, 113.09, 21.79, 18.94, 17.56.

EXAMPLE 7

1-(4-Amino-3-methylphenyl)-8-chloro-4-methyl-3-propionyl-3H-2,3-benzodiazepine 1.01 g (2.63 mmoles) 8-chloro-4-methyl-1-(3-methyl-4-nitrophenyl)-3-propionil-3H-2,3-benzodiazepine are dissolved in the mixture of 20 ml of methanol and 5 ml of dichloromethane, and about 0.5 g of wet Raney nickel catalyst and 0.33 ml (6.57 mmoles) of 98% hydrazine hydrate are subsequently added to it under vigorous stirring. The mixture is stirred for further 1 hour, the catalyst is filtered off, washed with dichloro-methane, the filtrate is evaporated and the residue is solidified by rubbing with 10 ml of water. The crude product is recrystallized from ethanol. Thus 0.51 g (55%) of the desired compound melting at 218-221° C. is obtained.

Elementary analysis: C$_{20}$H$_{20}$ClN$_3$O (353.85)
Calculated: C, 67.89%, H, 5.70%, N, 11.87%, Cl, 10.02%.
Found: C, 66.72%, H, 5.82%, N, 11.55%, Cl, 9.88%.
IR (KBr) 3352, 1639, 1323.
$^1$H-NMR (DMSO-d$_6$) δ 7.60 (dd, J1=2.3 Hz, J2=8.4 Hz, 1H), 7.45 (d, J=8.4 Hz, 1H), 7.25 (d, J=2.2 Hz, 1H), 6.95 (dd, J1=2.0 Hz, J2=8.3 Hz, 1H) 6.61 (d, J=8.3 Hz, 1H) 6.58 (s, 1H), 5.56 (bs, 2H), 2.60 (m, 1H), 2.35 (m, 1H), 2.16 (d, J=0.7 Hz, 3H), 2.06 (s, 3H), 0.98 (t, J=7.5 Hz, 3H).
$^{13}$C-NMR(DMSO-d$_6$) δ 171.26, 171.10, 150.11, 146.21, 137.86, 135.86, 131.85, 130.43, 130.32, 129.57, 129.47, 123.33, 122.85, 120.56, 113.07, 26.73, 18.97, 17.59, 8.77.

EXAMPLE 8

1-(4-Amino-3-methylphenyl)-8-chloro-4-methyl-3H-2,3-benzodiazepine-3-carboxylic acid methyl amide 10.89 g (28 mmoles) 8-chloro-4-methyl-1-(3-methyl-4-nitrophenyl)-3H-2,3-benzodiazepine 3-carboxylic acid methyl amide are dissolved in the mixture of 190 ml of methanol and 95 ml of dichloromethane, and about 5.0 g of wet Raney nickel catalyst and 3.5 ml (70 mmoles) of 98% hydrazine hydrate are subsequently added to it under vigorous stirring. The mixture is stirred for further 1 hour, the catalyst is filtered off, washed with dichloro-methane, the filtrate is evaporated and the residue is solidified by rubbing with 100 ml of water. The crude product is recrystallized from ethanol. Thus 7.73 g (78%) of the desired compound melting at 210-212° C. are obtained.

Elementary analysis: C$_{19}$H$_{19}$ClN$_4$O (354.838)
Calculated: C, 64.31%, H, 5.40%, N, 15.79%, Cl, 9.99%.
Found: C, 63.99%, H, 5.33%, N, 15.69%, Cl, 9.97%.
IR (KBr) 3465, 3397, 3378, 1668, 1507, 1318.

$^1$H-NMR (CDCl$_3$) δ 7.35 (dd, J1=2.2 Hz, J2=8.3 Hz, 1H), 7.21 (m, 2H), 7.16 (d, J=8.3 Hz, 1H), 7.07 (dd, J1=2.1 Hz, J2=8.3 Hz, 1H) 6.64 (d, J=8.2 Hz, 1H) 6.21 (s, 1H), 6.04 (bq, J=4.9 Hz, 1H), 3.93 (bs 2H) 2.94 (d, J=4.9 Hz, 3H), 2.24 (d, J=1.0 Hz, 3H), 2.18 (s, 3H),
$^{13}$C-NMR (CDCl$_3$) δ 169.67, 156.64, 147.72, 147.35, 138.52, 136.28, 131.79, 130.45, 130.30, 130.09, 129.49, 129.42, 125.98, 121.72, 121.60, 114.07, 26.78, 19.42, 17.28.

EXAMPLE 9

1-(4-Amino-3-methylphenyl)-8-chloro-4-methyl-3H-2,3-benzodiazepine-3-carboxylic acid cyclopropyl amide 1.38 g (3.35 mmoles) of 8-chloro-4-methyl-1-(3-methyl-4-nitrophenyl)-3H-2,3-benzodiazepine-3-carboxylic acid cyclopropyl amide is dissolved in the mixture of 28 ml of methanol and 14 ml of dichloromethane, and about 1.0 g of wet Raney nickel catalyst and 0.42 ml (8.37 mmoles) of 98% hydrazine hydrate are subsequently added to it under vigorous stirring. The mixture is stirred for further 1 hour, the catalyst is filtered off, washed with dichloromethane, the filtrate is evaporated and the residue is solidified by rubbing with 10 ml of water. The crude product is recrystallized from ethanol. Thus 1.15 g (90%) of the desired compound melting at 233-236° C. is obtained.

Elementary analysis: C$_{21}$H$_{21}$ClN$_4$O (380.876)
Calculated: C, 66.22%, H, 5.56%, N, 14.71%, Cl, 9.31%.
Found: C, 66.16%, H, 5.60%, N, 14.78%, Cl, 9.27%.
IR (KBr) 3394, 3333, 1669, 1506.
$^1$H-NMR (DMSO-d$_6$) δ 7.55 (dd, J1=2.0 Hz, J2=8.3 Hz, 1H), 7.37 (d, J=8.4 Hz, 1H), 7.21 (s, 1H), 7.16 (d, J=2.0 Hz, 1H), 7.04 (dd, J1=1.6 Hz, J2=8.2 Hz, 1H), 6.75 (bd, J=2.7 Hz, 1H), 6.59 (d, J=8.3 Hz, 1H), 6.37 (s, 1H), 5.47 (bs, 2H), 2.58 (m, 1H), 2.11 (s, 3H), 2.05 (s, 3H), 0.60 (m,4H).
$^{13}$C-NMR (DMSO-d$_6$) δ 168.73, 156.44, 149.69, 147.69, 138.49, 136.92, 132.08, 129.95, 129.78, 129.56, 129.14, 122.92, 121.47, 120.38, 112.96, 23.15, 19.07, 17.45, 6.42.

What we claim is:

1. A compound of the formula (I)

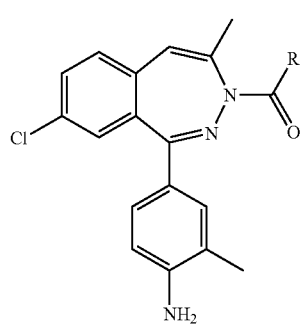

(I)

wherein
R is a lower alkyl group or —NHR$^1$, wherein
R$^1$ is a lower alkyl or a lower cycloalkyl group, or a pharmaceutically acceptable acid addition salt thereof.

2. The compound of the formula (I) as defined in claim 1, wherein R is C$_1$ to C$_4$ alkyl, or a pharmaceutically acceptable acid addition salt thereof.

3. The compound of the formula (I) as defined in claim 2, wherein R is methyl or ethyl, or a pharmaceutically acceptable acid addition salt thereof.

4. The compound of the formula (I) as defined in claim 1, wherein R is —NHR$^1$, and R$^1$ is a C$_1$ to C$_4$ alkyl or a C$_3$ to C$_6$ cycloalkyl group, or a pharmaceutically acceptable acid addition salt thereof.

5. The compound of the formula (I) as defined in claim 4, wherein R$^1$ is a methyl or a cyclopropyl group, or a pharmaceutically acceptable acid addition salt thereof.

6. The compound of the formula (I) as defined in claim 1, selected from the group consisting of:
  (a) 1-(4-amino-3-methylphenyl)-8-chloro- 4-methyl-3H-2,3-benzodiazepine 3-carboxylic acid methyl amide;
  (b) 1-(4-amino-3-methylphenyl)-8-chloro-4-methyl-3H-2,3- benzodiazepine-3-carboxylic acid cyclopropyl amide;
  (c) 3-acetyl-1-(4-amino-3-methylphenyl)-8-chloro-4-methyl-3H-2,3-benzodiazepine; and
  (d) 3-propionyl-1-(4-amino-3-methylphenyl)-8-chloro-4-methyl-3H-2,3-benzodiazepine, or a pharmaceutically acceptable acid addition salt thereof.

7. A process for the preparation of a compound of the formula (I)

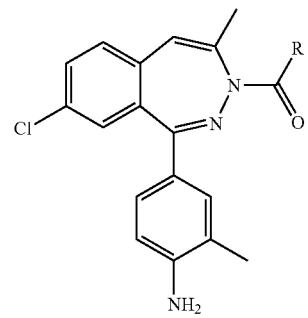

(I)

wherein
R is a C$_1$ to C$_6$ alkyl group or —NHR$^1$, wherein
R$^1$ is a C$_1$ to C$_6$ alkyl or a C$_3$ to C$_7$ cycloalkyl group, or a pharmaceutically acceptable acid addition salt thereof, which comprises
(a) reducing a compound of the formula (II),

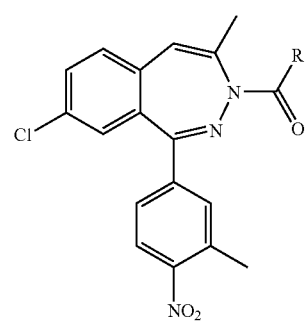

(II)

wherein R is as stated above; or
for the preparation of a compound of the formula (I) wherein R is specifically —NHR$^1$ wherein R$^1$ is as stated above, (b) reacting a compound of the formula (IV),

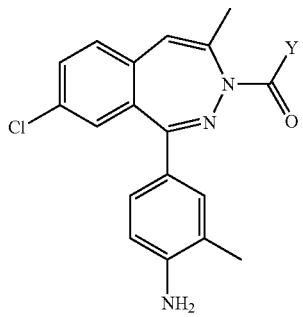 (IV)

wherein Y is a lower alkyl group or a leaving group, with a compound of the formula (V),

H₂N—R¹  (V)

wherein R¹ is as stated above, and, if desired, converting the compound of the formula (I) thus obtained into a pharmaceutically acceptable acid addition salt thereof.

8. A pharmaceutical composition for treating cerebral ischemia comprising as active ingredient a therapeutically effective amount of the compound of the formula (I) as defined in claim 1 or a pharmaceutically acceptable acid addition salt thereof in admixture with an inert solid or liquid carriers and/or auxiliary agent.

9. A method of treating a patient suffering from cerebral ischemia to protect the patient from neuronal loss, which comprises the step of administering to said patient in need of such treatment, a therapeutically effective amount of the compound of the formula (I) as defined in claim 1 or a pharmaceutically acceptable acid addition salt thereof.

10. A compound of the formula (II)

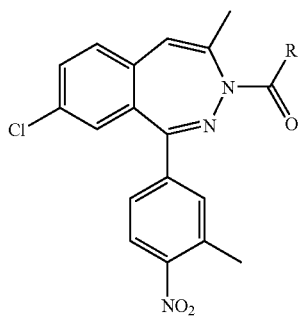 (II)

wherein R is a lower alkyl group or —NHR¹, wherein
R¹ is a lower alkyl or a lower cycloalkyl group, or a pharmaceutically acceptable acid addition salt thereof.

11. compound of the formula (VIII)

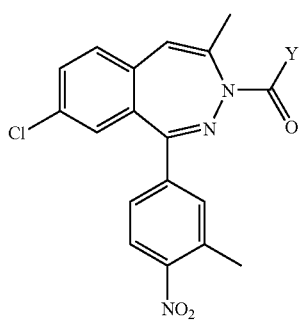 (VIII)

wherein Y is a leaving group.

12. A process for the preparation of a compound of the formula (II)

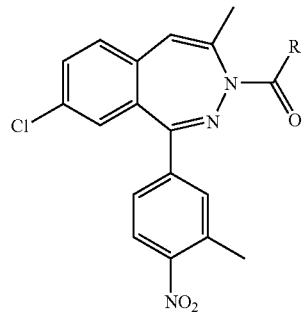 (II)

wherein
R is a lower alkyl group or —NHR¹, wherein
R¹ is a lower alkyl or a lower cycloalkyl group, or a pharmaceutically acceptable acid addition salt thereof, which comprises the steps of: reacting a compound of the formula (VII)

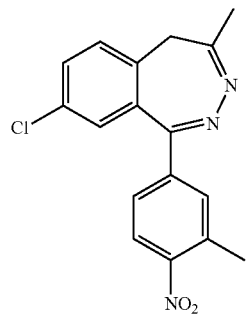 (VII)

with a reagent capable of introducing a Y group, and reacting the thus-obtained compound of the formula (VIII)

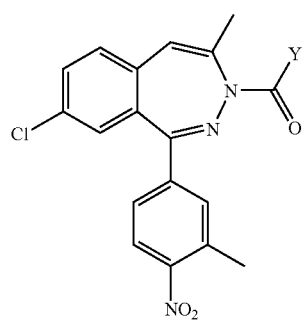 (VIII)

with a compound of the formula (V)

H₂N—R¹  (V)

to obtain the desired product.

* * * * *